(12) United States Patent
Dahlmann et al.

(10) Patent No.: US 7,214,276 B2
(45) Date of Patent: May 8, 2007

(54) ETHER CARBOXYLIC ACIDS BASED ON ALKOXYLATED STYRYLPHENOLS

(75) Inventors: Uwe Dahlmann, Heidelberg (DE); Rainer Kupfer, Hattersheim (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 300 days.

(21) Appl. No.: 10/988,294

(22) Filed: Nov. 12, 2004

(65) Prior Publication Data

US 2005/0107281 A1    May 19, 2005

(30) Foreign Application Priority Data

Nov. 17, 2003 (DE) ................ 103 53 603

(51) Int. Cl.
- C23G 5/032 (2006.01)
- B08B 7/00 (2006.01)
- C11D 3/37 (2006.01)

(52) U.S. Cl. .............. 134/41; 134/38; 134/42; 510/245; 510/360; 510/413; 510/434; 510/475; 510/476; 510/477; 510/488

(58) Field of Classification Search ........ 510/245, 510/360, 413, 434, 475, 476, 477, 488; 8/137; 134/38, 41, 42
See application file for complete search history.

(56) References Cited

U.S. PATENT DOCUMENTS

| 4,399,050 A | 8/1983 | Bentham et al. |
| 4,607,121 A | 8/1986 | Faggian et al. |
| 6,326,514 B1 | 12/2001 | Klug et al. |
| 2003/0194388 A1 | 10/2003 | Dahlmann et al. |
| 2004/0152600 A1 | 8/2004 | Dahlman et al. |

FOREIGN PATENT DOCUMENTS

| DE | 10123210 | 10/2002 |
| JP | 06235190 A * | 8/1994 |

OTHER PUBLICATIONS

English Abstract and Machine Translation of Japanese Publication JP 06235190.

English Abstract and Machine Translation of Japanese Publication JP 2002241789.

English Abstract and Machine Translation of Japanese Publication JP 08245499.

English Abstract and Machine Translation of Japanese Publication JP 07277796.

English Abstract of Japanese Publication JP 02 151619, Jun. 11, 1990.

English Abstract of Japanese Publication JP 10 270846, Oct. 9, 1998.

English Abstract and Machine translation of Japanese Publication JP 06235190, (Aug. 23, 1994)—Previously Submitted in IDS filed Feb. 3, 2005.

English Abstract and Machine translation of Japanese Publication JP 2002241789, (Aug. 28, 2002)—Previously Submitted in IDS filed Feb. 3, 2005.

English Abstract and Machine translation of Japanese Publication JP 08245499, (Sep. 24, 1996)—Previously Submitted in IDS filed Feb. 3, 2005.

English Abstract and Machine translation of Japanese Publication JP 07277796, (Oct. 24, 1995)—Previously Submitted in IDS filed Feb. 3, 2005.

* cited by examiner

Primary Examiner—Brian Mruk
(74) Attorney, Agent, or Firm—Richard P. Silverma

(57) ABSTRACT

The invention relates to compounds of the formula (1)

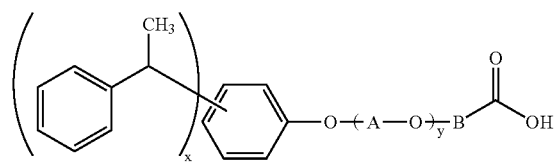

(1)

in which
A is $C_2$- to $C_4$-alkylene,
B is $C_1$- to $C_4$-alkylene,
x is a number from 1 to 3, and
y is a number from 1 to 100.

8 Claims, No Drawings

ETHER CARBOXYLIC ACIDS BASED ON ALKOXYLATED STYRYLPHENOLS

The present invention relates to ether carboxylic acids based on alkoxylated styrylphenols, to their preparation, and to their use as surface-active additives.

Ether carboxylic acids, i.e. organic carboxylic acids, which carry one or more ether bridges besides the carboxyl function, and/or alkali metal or amine salts thereof are known as mild nonionic and/or anionic detergents with high lime soap dispersing power. They are used both in detergent and cosmetic formulations, but also in industrial applications (e.g. metal working fluids, cutting fluids, industrial cleaners, additives for textile and leather processing, auxiliaries in papermaking and pulp preparation).

These products are prepared in accordance with the prior art either by alkylation of alcohol or fatty alcohol oxyethylates or oxypropylates with chloroacetic acid derivatives (Williamson's ether synthesis) or from the same starting materials by oxidation with various reagents (atmospheric oxygen, hypochlorite, chlorite) with catalysis by various catalysts.

DE-C-199 28 128 discloses a process for the preparation of ether carboxylic acids with a low residual alcohol content by firstly reacting fatty alcohols with alkylene oxides using non-catalytic amounts of alkali metal catalyst (NaOH, KOH, alkoxides above 5 mol %), and then converting the resulting highly alkaline reaction mixtures, which consist of a mixture of oxyethylated alcohols and alkoxides of different poly-alkylene glycol ethers, into the corresponding ether carboxylic acid in a classic Williamson synthesis with sodium chloroacetate. This reduces the residual content of fatty alcohol in the ether carboxylic acid without special catalysts.

DE-C-10123210 discloses ether carboxylic acids based on alkoxylated 2-mercaptobenzothiazoles which have good film formation and film persistence and are therefore used as corrosion-inhibiting agents for metal working, and also for the recovery and processing of crude oil and natural gas.

The use of ether carboxylic acids as surface-active additives depends heavily on their ability to simultaneously have excellent wetting behavior, for example on fiber surfaces, besides good emulsifier properties and lime soap dispersing power, and, with regard to corrosion protection and lubricating properties, to form films on metal surfaces which are persistent even during considerable mechanical stress, such as during grinding, cutting and boring of metal workpieces and/or under high flow rates and pressures.

These properties have been satisfied adequately by ether carboxylic acids of the prior art based on alkoxylated alkylphenols (APEs), primarily alkoxylated nonylphenols (NPEs). However, according to the European Directives 2003/53/EC and 76/769/EEC Appendix I No. 46, NPEs have an increased hazard potential for people and the environment and must therefore no longer be put into circulation in concentrations above 0.1% by mass.

It was therefore the object to find novel, alternative substances to ether carboxylic acids based on NPEs which do not have an increased hazard potential and exhibit comparable or improved surface-active properties.

Surprisingly, it has been found that ether carboxylic acids based on alkoxylated styrylphenols (1-phenylethylphenols) have excellent emulsifier properties with high lime soap dispersing power and excellent film formation, and also very good ecotoxicological properties.

The invention therefore provides compounds of the formula (1)

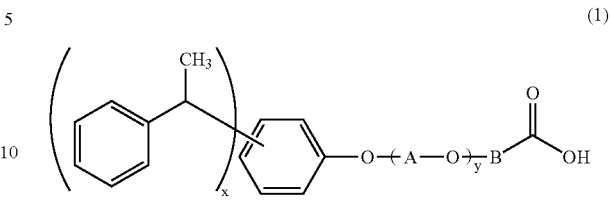

in which
A is $C_2$- to $C_4$-alkylene,
B is $C_1$- to $C_4$-alkylene,
x is a number from 1 to 3, and
y is a number from 1 to 100.

The invention further provides the use of the compounds of the formula 1 as surface-active ingredient, preferably in metal working compositions, industrial cleaners and auxiliaries for textile, leather and paper processing.

The invention further provides a process for the preparation of a surface-active composition by adding the compound of the formula 1 to a composition without surface-active properties.

A is preferably propylene or ethylene, in particular ethylene. In a further preferred embodiment of the invention, the group $(A-O)_y$ is a mixed alkoxy group which can contain ethylene, propylene and butylene radicals. If this is a mixed alkoxy group, then the molar ratio of the groups derived from ethylene oxide to the groups derived from propylene oxide or butylene oxide is preferably between 10:1 and 1:1.

y is preferably a number between 2 and 70, in particular 3 to 50.

x is preferably 2 or 3, in particular 3.

The invention further provides salts of the compounds of the formula (1) corresponding to formula (2)

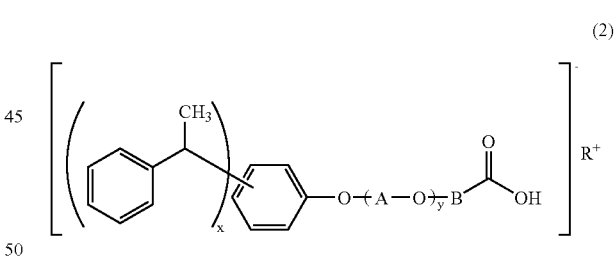

in which
A is $C_2$- to $C_4$-alkylene,
B is $C_1$- to $C_4$-alkylene,
x is a number from 1 to 3,
y is a number from 1 to 100, and
$R^+$ is a cation.

The invention further provides the use of the compounds of the formula 2 as surface-active ingredient, preferably in metal working compositions, industrial cleaners and auxiliaries for textile, leather and paper processing.

The invention further provides a process for the preparation of a surface-active composition by adding the compound of the formula 2 to a composition without surface-active properties.

A, B, x and y have the meanings already given above.

In a preferred embodiment, R is alkali metal or alkaline earth metal ions, in particular lithium, sodium, potassium, magnesium or calcium.

In a further preferred embodiment, the cations used are ammonium ions of the formula $NR^1R^2R^3R^4$, where $R^1$, $R^2$, $R^3$ and $R^4$, independently of one another, may be H, $C_1$- to $C_{22}$-alkyl, $C_6$- to $C_{18}$-aryl, $C_7$- to $C_{22}$-alkylaryl and/or $C_1$- to $C_{22}$-alkenyl. The radicals $R^1$, $R^2$, $R^3$ and $R^4$ may contain heteroatoms such as N, P, O, S. The ammonium radicals may be monoalkylammonium, dialkylammonium, trialkylammonium or tetraalkylammonium radicals in which the alkyl substituents, independently of one another, may be occupied by up to 3 hydroxyl groups. R is preferably ammonium radicals which carry one, two, three or four $C_2$- to $C_{10}$-alkyl radicals. In a further preferred embodiment, one, two or three of the radicals $R^1$ to $R^4$ may be alkoxylated.

Suitable amines for the preparation of ammonium cations R are monoamines with primary or secondary amino function, such as methylamine, ethylamine, butylamine, laurylamine, coconut fatty amine, stearylamine, dimethylamine, diethylamine, dibutylamine, but also di- and polyamines, such as, for example, 3-dimethylamino-propylamine, 3-diethylaminopropylamine, 3-morpholinopropylamine, diethylenetriamine, triethylenetetramine or tetraethylenepentamine.

Suitable amino alcohols for the preparation of ammonium cations R are, for example, N,N-dimethylaminoethanol, N,N-diethylaminoethanol, N,N-dibutylaminoethanol, 3-dimethylaminopropanol, N-hydroxyethylmorpholine, monoethanolamine, diethanolamine, triethanolamine, 3-aminopropanol, isopropanolamine, 2(2-aminoethoxy)ethanol and cyclohexylamino-N,N-diethanol.

Suitable amine alkylthiols for the preparation of ammonium cations R are cysteamine and cystamine.

The compounds of the formula 1 according to the invention can be prepared by firstly alkoxylating styrylphenols and then reacting with monochlorocarboxylic acids. The term styrylphenol encompasses mono-, di- and tristyrylphenols (mono-, di- and tri(1-phenylethyl)phenols) and mixtures thereof.

Styrylphenols can be prepared according to the prior art by Friedel-Crafts alkylation of phenol. Preferred substitution takes place in the o- and p position.

Styrylphenol is generally reacted with ethylene oxide, propylene oxide, butylene oxide or mixtures of different alkylene oxides of this type, preference being given to ethylene oxide or mixtures of ethylene oxide and propylene oxide. Based on styrylphenol, 1–100 mol of alkylene oxide are supplied, preferably 2–70 mol, particularly preferably 3–50 mol.

The alkoxylation generally takes place without the use of solvents. If solvents are used, preference is given to inert ethers, such as dioxane, tetrahydrofuran, glyme, diglyme and MPEGs. Water as well as alcohols, such as propanols, butanols, and oxyethylated monoalcohols, such as butyl glycol, isobutyl glycol and butyl diglycol, can be used, but lead to a high content of by-products.

Basic compounds which can be used for the preparation of the oxyethylated styrylphenol are alkaline earth metal/alkali metal hydroxides or alkoxides (sodium methoxide, sodium ethoxide, potassium tert-butoxide), but preference is given to alkali metal hydroxides, particularly sodium hydroxide or potassium hydroxide.

The basic compounds are used in amounts of about 5–95 mol %, based on styrylphenol, preferably between 15 and 90 mol %, particularly preferably between 20–60 mol %.

Starting from the styrylphenol, the phenoxide necessary for the oxyalkylation is prepared by reaction with the basic compounds. In order to avoid relatively high contents of by-products (glycols, glycol ethers of lower alcohol) in the end product, the water of reaction which forms in the process or the corresponding lower alcohol should be removed from the reaction mixture prior to the reaction with the alkylene oxide. This can either be achieved by reacting the styrylphenol with an alkali metal hydroxide and distilling off the water of reaction, or by reacting the base alcohol with an alkoxide of a lower alcohol and distilling off the lower alcohol. On the other hand, styrylphenol can be monoalkoxylated in a two-step process, in the first step without the addition of the basic compounds. In a further step, the necessary reaction to the alkoxide then takes place.

The resulting mixture of styrylphenol and the corresponding styrylphenoxide and/or styrylphenyl alkoxylate is then reacted with about 1–100 mol of an alkylene oxide, preferably ethylene oxide and/or propylene oxide, the reaction temperatures here are about 80 to 160° C. Here, in the case of a reaction catalyzed with relatively high amounts of alkali, a relatively narrow homolog distribution arises.

In the subsequent reaction step, the styrylphenyl-oxyalkylate mixture is reacted with a chlorocarboxylic acid derivative and a base, preferably dry sodium chloroacetate and sodium hydroxide. This may be brought about by reacting the oxyalkylate mixture with 100 to 150 mol % of sodium chloroacetate at 30 to 100° C. and, simultaneously or subsequently, adding solid sodium hydroxide or potassium hydroxide, such that the sum of the base already present in the oxyalkylate mixture and the amount of base additionally added corresponds to the amount of sodium chloroacetate. The amount of base already present from the reaction with the alkylene oxide can thus be used directly for the subsequent Williamson synthesis and does not have to be washed out, as in the case of the synthesis of a standard oxyalkylate.

After the alkylation reaction, the resulting solution of the styrylphenyl-ether carboxylic acid alkali metal salt can either be used directly as compound according to the invention, or be converted to the free styrylphenyl-ether carboxylic acid. For this purpose, the mixture is acidified to pH <3 using strong mineral acid (hydrochloric acid, sulfuric acid), and the styrylphenyl-ether carboxylic acid is separated off hot as upper phase by phase separation above its cloud point.

The free ether carboxylic acids according to the invention can also be prepared directly by oxidation of the styrylphenyl-oxyalkylate mixture with various reagents (atmospheric oxygen, hypochlorite, chlorite) with catalysis by various catalysts. Particular preference is given to the oxidation by means of oxygen using supported platinum catalysts.

The oxidation can be carried out with or without the use of solvents.

The oxidation takes place at temperatures of from 10 to 250° C., preferably at 20 to 1 50° C., particularly preferably at 50 to 100° C.

The styrylphenyl-ether carboxylic acid ammonium salts according to the invention are generally prepared by directly reacting the free acid with the correspondingly functionalized amines at temperatures below 60° C.

EXAMPLES

Example 1 (Tristyrylphenol+5 EO)

812 g of tristyrylphenol were initially introduced into a 2 l ethoxylation autoclave under nitrogen blanketing and gassed with ethylene oxide at 120 to 130° C. with NaOH catalysis (1%) until 10 mol of EO had reacted under pressure constancy. The mixture was after-reacted for 1 h at 150° C. Distilling off readily volatile components produced the product as a clear colorless liquid. According to the OH number, the average EO content was 4.5. The cloud point was determined as 23° C.

Example 2 (Tristyrylphenol+10 EO)

609 g (1.5 mol) of tristyrylphenol were initially introduced into a 2 l ethoxylation autoclave under nitrogen blanketing and gassed with ethylene oxide at 120 to 130° C. with NaOH catalysis (1%) until 15 mol of EO had reacted with pressure constancy. The mixture was after-reacted for 1 h at 150° C. Distilling off readily volatile components produced the product as a clear colorless liquid. According to the OH number, the average EO content was 10.5. The cloud point was determined as 68° C.

Example 3 (Tristyrylphenol+5 EO-ECS)

596 g of tristyrylphenol+5 EO (1 mol corresponding to OH number) were initially introduced into a 2 l stirred apparatus under nitrogen blanketing and heated to 40° C. 140 g (1.2 mol) of sodium chloroacetate were then introduced and the reaction mixture was heated to 50° C. After 30 min in each case, 48 g (1.2 mol) of NaOH microprills were added in 4 portions such that the temperature did not exceed 50–60° C. The mixture was after-reacted for 2 h at 80–100° C. 440 g of 10% hydrochloric acid were then allowed to run in, the mixture was heated to 95° C. and transferred to a heatable stirred apparatus with bottom outlet. Phase separation took place after 30 min at 105° C., with 560 g of aqueous lower phase being separated off and 660 g of tristyrylphenol+10 EO-ECS with a water content of 4.5% being obtained.

Example 4 (Tristyrylphenol+10 EO-ECS)

866 g of tristyrylphenol+5 EO (1 mol corresponding to OH number) were initially introduced into a 2 l stirred apparatus under nitrogen blanketing and heated to 40° C. 140 g (1.2 mol) of sodium chloroacetate were then introduced and the reaction mixture was heated to 50° C. After 30 min in each case, 48 g (1.2 mol) of NaOH microprills were added in 4 portions such that the temperature did not exceed 50–60° C. The mixture was after-reacted for 2 h at 80–100° C. 440 g of 10% hydrochloric acid were then allowed to run in, the mixture was heated to 95° C. and transferred to a heatable stirred apparatus with bottom outlet. Phase separation took place after 15 min at 105° C., with 535 g of aqueous lower phase being separated off and 955 g of tristyrylphenol+10 EO-ECS with a water content of 6.5% being obtained.

Use of the compounds according to the invention as surface-active additive for water-miscible cutting fluids, cleaning liquids and surface treatments.

The compounds according to the invention can be used in the form of milky-opal and semisynthetic (transparent) emulsions or completely synthetic (oil-free) solutions for water-miscible cutting fluids, cleaning liquids and surface treatments. The use concentrations are 1 to 50%, preferably 2 to 10%, particular preferably 3 to 5%.

The compounds according to the invention can be used in any ratios with emulsifiers and coemulsifiers (anionic ones, for example sulfonates, carboxylic acids, ether carboxylic acids); (nonionic ones, for example alkyl alkoxylates, mono- and polyvalent alcohols), corrosion inhibitors (for example alkenylsuccinic acid derivatives, sulfonates, mono- and polyvalent carboxylic acids, ether carboxylic acids, fatty acid amides, amines, heterocyclic compounds and boric acid), lubricants (for example natural and synthetic fats and oils, fatty acids, esters and amides, polymers), EP/AW additives (extreme pressure/anti-wear; for example sulfur compounds, phosphoric esters, dithiophosphates and molybdenum compounds), biocides (for example boric acid, formaldehyde-releasing substances and heterocyclic compounds), chelating agents and sequestering agents (for example alkanolamines, amino carboxylic acids), antifoams (for example silicone and fluorine compounds), antimisting additives and base liquids (for example mineral oils, synthetic and natural esters and polyesters, polyalkylene glycols, and water).

The effectiveness of the compounds according to the invention as emulsifier was tested using a guide formulation for transparent emulsions (concentrate: 40% mineral oil, 40% corrosion inhibitor package, 5% emulsifiers, 10% water and 5% ether carboxylic acid to be tested). Here, both the stability of the concentrate (at T=0° C., 20° and 40° C.), and also that of the emulsion (5% concentrate in DIN water 20° German hardness) was assessed visually following preparation and after 24 h. The compounds according to the invention produced stable concentrates and emulsions.

The corrosion protection test was carried out in accordance with the DIN Standard 51360, Part 2 (filter paper test) and serves to assess the corrosion of iron metal. A measure of the corrosion is the type and number of corrosion marks on a round filter which form as a result of the action of a cutting fluid (CF) mixed with water on standardized grey iron turnings (turning size: 3 to 6 mm$^2$). The assessment is made by means of a visual test and grading of the degree of corrosion (1 to 4) according to a comparison table.

The comparison used was commercially available emulsifiers (Emulsogen® COL 050 and COL 100) with comparable degree of alkoxylation. These are essentially ether carboxylic acids of the composition oleyl-O-(EO)$_5$-CH$_2$-COOH (Emulsogen COL 050) or the homolog with 10 EO groups (Emulsogen COL 100).

The tested additives were adjusted to pH 8.9 with triethanolamine (TEA) to form the corresponding ammonium salt.

TABLE 1

Corrosion protection test in accordance with DIN (filter paper test)

| Example | Emulsifier/corrosion inhibitor | Concentration of the corrosion inhibitor | | |
|---|---|---|---|---|
| | | 2% | 3% | 4% |
| 5 (C) | Emulsogen COL 050 | 1–2 | 0–1 | 0 |
| 6 (C) | Emulsogen COL 100 | 4 | 3 | 2–3 |
| 7 | from Example 3 | 2 | 0–1 | 0 |
| 8 | from Example 4 | 3 | 1 | 1 |

The lime soap dispersing power of the compounds according to the invention was tested in accordance with the DIN Standard 53903 and is used to assess the ability of keeping the precipitations (lime soaps) caused by the water hardness formers in solution. A measure of the lime soap dispersing power is the K value, which gives the ratio of the dispersed amount of lime soap, calculated as 100% sodium oleate, per 1 g of emulsifier. As comparison, the abovementioned emulsifiers (Example 5 and 6) were likewise used.

TABLE 2

| | Lime soap dispersing power in accordance with DIN | |
|---|---|---|
| Example | Emulsifier/corrosion inhibitor | K value |
| 9 (C) | Emulsogen COL 050 | 17 |
| 10 (C) | Emulsogen COL 100 | 33 |
| 11 | from Example 3 | 11 |
| 12 | from Example 4 | 20 |

The invention claimed is:

1. A process for forming a film on a metal surface, said process comprising contacting the metal surface with a water-miscible fluid comprising the compound of the formula (1)

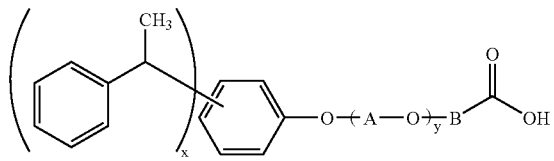

(1)

in which
   A is $C_2$- to $C_4$-alkylene,
   B is $C_1$- to $C_4$-alkylene,
   x is a number from 1 to 3, and
   y is a number from 1 to 100.

2. The process of claim 1, wherein the water-miscible fluid is selected from the group consisting of cutting fluid, cleaning liquid, and surface treatment fluid.

3. The process of claim 1, in which A is propylene or ethylene.

4. The process of claim 1, in which the group $(A-O)_y$ is a mixed alkoxy group having a radical selected from the group consisting of ethylene, propylene, butylenes, and mixtures thereof.

5. The process of claim 1, in which the group $(A-O)_y$ is a mixed alkoxy group which contains ethylene, propylene and butylene radicals, and in which the molar ratio of the groups derived from ethylene oxide to the groups derived from propylene oxide or butylene oxide is between 10:1 and 1:1.

6. The process of claim 1, in which y is a number between 2 and 70.

7. The process of claim 1, in which x is 2 or 3.

8. The process of claim 1, in which the compound of formula (1) is in the form of a salt according to formula (2)

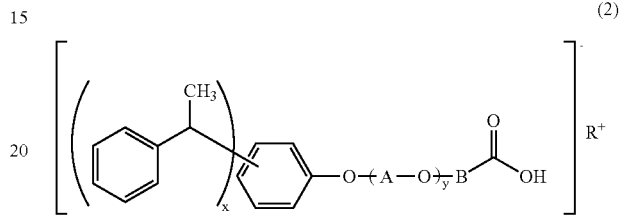

(2)

in which
   A is $C_2$- to $C_4$-alkylene,
   B is $C_1$- to $C_4$-alkylene.
   x is a number from 1 to 3, and
   y is a number from 1 to 100, and
   R is an ammonium ion of the formula $NR^1R^2R^3R^4$, where $R^1$, $R^2$, $R^3$ and $R^4$, independently of one another, are selected from the group consisting of H, $C_1$- to $C_{22}$-alkyl, $C_6$- to $C_{18}$-aryl, $C_7$- to $C_{22}$-alkylaryl, $C_1$- to $C_{22}$-alkenyl, and mixtures thereof, which may contain heteroatoms selected from the group consisting of N, P, O, S, and mixtures thereof.

\* \* \* \* \*